(12) United States Patent
Ewers et al.

(10) Patent No.: US 7,377,898 B2
(45) Date of Patent: May 27, 2008

(54) WOUND RETRACTION APPARATUS AND METHOD

(75) Inventors: Richard C Ewers, Fullerton, CA (US); John R Brustad, Dana Point, CA (US); Edward D Pingleton, San Juan Capistrano, CA (US); Nabil Hilal, Laguna Niguel, CA (US); Payam Adlparvar, Lake Forest, CA (US); Scott V Taylor, Mission Viejo, CA (US); Gary R Dulak, Valencia, CA (US); Michael J Dunn, Santa Ana, CA (US); Norman L Morales, Daly City, CA (US); Charles C Hart, Summerville, SC (US); Robert R Bowes, Laguna Hills, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 11/755,305

(22) Filed: May 30, 2007

(65) Prior Publication Data

US 2007/0225569 A1    Sep. 27, 2007

Related U.S. Application Data

(63) Continuation of application No. 11/218,412, filed on Sep. 1, 2005, now Pat. No. 7,238,154, which is a continuation of application No. 10/399,209, filed on Aug. 22, 2003, now Pat. No. 6,958,037.

(51) Int. Cl.
    *A61B 1/32* (2006.01)

(52) U.S. Cl. .................................................. 600/208

(58) Field of Classification Search ........ 600/206–208; 606/213, 215, 216
    See application file for complete search history.

(56) References Cited

U.S. PATENT DOCUMENTS 1,810,466 A    6/1931    Deutsch (Continued)

FOREIGN PATENT DOCUMENTS

EP    1 125 552    8/2001

(Continued)

OTHER PUBLICATIONS

Dexterity Protractor Instruction Manual by Dexterity Surgical, Inc.
Horigane, et al , Technical Note: Development of a Duodoenal Cannula for Sheep, Journal of Animal Science, Apr. 1992, vol. 70, Issue 4, pp. 1216-1219.

(Continued)

*Primary Examiner*—Cary E. O'Connor
(74) *Attorney, Agent, or Firm*—David G. Majdali (57) ABSTRACT

A surgical wound retractor is adapted to dilate a wound stretchable to a desired diameter, the retractor includes a first ring having a diameter greater than that desired for the wound and being adapted for disposition interiorly of the wound. A second ring has a diameter greater than that desired for the wound and is adapted for disposition exteriorly of the wound. A plurality of retraction elements are disposed in a generally cylindrical relationship to each other, between the first ring and the second ring. These elements extend through the wound to exert a radial retraction force on the wound which is dependent on the distance separating the first ring and the second ring Retraction elements, both distensible and non-distensible are contemplated with appropriate attachment means at the rings to provide for variations in the retraction force. With a suitable retraction sleeve, a third ring can be provided to form a circumferential retainer to vary the retraction force. Rings can also be made inflatable or self-expanding to vary the retraction force. An associated method includes the step of rolling the second ring circumferentially of the third ring to form the circumferential retainer.

2 Claims, 12 Drawing Sheets

U.S. PATENT DOCUMENTS

| | | |
|---|---|---|
| 2,305,289 A | 12/1942 | Coburg |
| 2,835,253 A | 5/1958 | Borgeson |
| 2,853,075 A | 9/1958 | Hoffman et al. |
| 3,039,468 A | 6/1962 | Price |
| 3,111,943 A | 11/1963 | Orndorff |
| 3,244,169 A | 4/1966 | Baxter |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,523,534 A | 8/1970 | Nolan |
| 3,717,151 A | 2/1973 | Collett |
| 3,841,332 A | 10/1974 | Treacle |
| 3,850,172 A | 11/1974 | Cazalis |
| 3,856,021 A | 12/1974 | McIntosh |
| 4,024,872 A | 5/1977 | Muldoon |
| 4,043,328 A | 8/1977 | Cawood, Jr. et al. |
| 4,069,913 A | 1/1978 | Harrigan |
| 4,083,370 A | 4/1978 | Taylor |
| 4,188,945 A | 2/1980 | Wenander |
| 4,217,664 A | 8/1980 | Faso |
| 4,222,126 A | 9/1980 | Boretos et al. |
| 4,338,937 A | 7/1982 | Lerman |
| 4,367,728 A | 1/1983 | Mutke |
| 4,550,713 A | 11/1985 | Hyman |
| 4,553,537 A | 11/1985 | Rosenberg |
| 4,714,749 A | 12/1987 | Hughes et al. |
| 4,755,170 A | 7/1988 | Golden |
| 4,777,943 A | 10/1988 | Chvapil |
| 4,863,438 A | 9/1989 | Gauderer et al. |
| 4,895,565 A | 1/1990 | Hillstead |
| 4,903,710 A | 2/1990 | Jessamine et al. |
| 4,926,882 A | 5/1990 | Lawrence |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,015,228 A | 5/1991 | Columbus et al. |
| 5,037,379 A | 8/1991 | Clayman et al. |
| 5,082,005 A | 1/1992 | Kaldany |
| 5,178,162 A | 1/1993 | Bose |
| 5,192,301 A | 3/1993 | Kamiya et al. |
| 5,213,114 A | 5/1993 | Bailey, Jr. |
| 5,299,582 A | 4/1994 | Potts |
| 5,316,541 A | 5/1994 | Fischer |
| 5,350,364 A | 9/1994 | Stephens et al. |
| 5,353,786 A | 10/1994 | Wilk |
| 5,366,478 A | 11/1994 | Brinkerhoff et al. |
| 5,368,545 A | 11/1994 | Schaller et al. |
| 5,380,288 A | 1/1995 | Hart et al. |
| 5,389,080 A | 2/1995 | Yoon |
| 5,389,081 A | 2/1995 | Castro |
| 5,407,433 A | 4/1995 | Loomas |
| 5,429,609 A | 7/1995 | Yoon |
| 5,437,683 A | 8/1995 | Neumann et al. |
| 5,460,616 A | 10/1995 | Weinstein et al. |
| 5,476,475 A | 12/1995 | Gadberry |
| 5,480,410 A | 1/1996 | Cuschieri et al. |
| 5,492,304 A | 2/1996 | Smith et al. |
| 5,496,280 A | 3/1996 | Vandenbroek et al. |
| 5,503,112 A | 4/1996 | Luhman et al. |
| 5,514,133 A | 5/1996 | Golub et al. |
| 5,522,791 A | 6/1996 | Leyva |
| 5,524,644 A | 6/1996 | Crook |
| 5,531,758 A | 7/1996 | Uschold et al. |
| 5,545,179 A | 8/1996 | Williamson, IV |
| 5,562,677 A | 10/1996 | Hildwein et al. |
| 5,603,702 A | 2/1997 | Smith et al. |
| 5,628,732 A | 5/1997 | Antoon, Jr. et al. |
| 5,632,284 A | 5/1997 | Graether |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,672,168 A | 9/1997 | de la Torre et al. |
| 5,681,341 A | 10/1997 | Lunsford et al. |
| 5,709,664 A | 1/1998 | Vandenbroek et al. |
| 5,720,730 A | 2/1998 | Blake, III |
| 5,728,103 A | 3/1998 | Picha et al. |
| 5,741,298 A | 4/1998 | MacLeod |
| 5,782,817 A | 7/1998 | Franzel et al. |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,810,721 A | 9/1998 | Mueller et al. |
| 5,813,409 A | 9/1998 | Leahy et al. |
| 5,814,026 A | 9/1998 | Yoon |
| 5,832,925 A | 11/1998 | Rothrum |
| 5,841,298 A | 11/1998 | Huang |
| 5,853,395 A | 12/1998 | Crook et al. |
| 5,865,729 A | 2/1999 | Meehan et al. |
| 5,865,807 A | 2/1999 | Blake, III |
| 5,895,377 A | 4/1999 | Smith et al. |
| 5,899,208 A | 5/1999 | Bonadio |
| 5,904,703 A | 5/1999 | Gilson |
| 5,906,577 A | 5/1999 | Beane et al. |
| 5,947,922 A | 9/1999 | MacLeod |
| 5,964,781 A | 10/1999 | Mollenauer et al. |
| 5,989,233 A | 11/1999 | Yoon |
| 5,993,471 A | 11/1999 | Riza et al. |
| 5,993,485 A | 11/1999 | Beckers |
| 5,997,515 A | 12/1999 | de la Torre et al. |
| 6,010,494 A | 1/2000 | Schafer et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,045,535 A | 4/2000 | Ben Nun |
| 6,142,936 A | 11/2000 | Beane et al. |
| 6,149,642 A | 11/2000 | Gerhart et al. |
| 6,162,172 A | 12/2000 | Cosgrove et al. |
| 6,254,533 B1 | 7/2001 | Fadem et al. |
| 6,254,534 B1 | 7/2001 | Butler et al. |
| 6,382,211 B1 | 5/2002 | Crook |
| 6,383,162 B1 | 5/2002 | Sugarbaker |
| 6,413,244 B1 | 7/2002 | Bestetti et al. |
| 6,440,063 B1 | 8/2002 | Beane et al. |
| 6,450,983 B1 | 9/2002 | Rambo |
| 6,482,181 B1 | 11/2002 | Racenet et al. |
| 6,485,435 B1 | 11/2002 | Bakal |
| 6,533,734 B1 | 3/2003 | Corley, III et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,613,952 B2 | 9/2003 | Rambo |
| 6,623,426 B2 | 9/2003 | Bonadio et al. |
| 6,702,787 B2 | 3/2004 | Racenet et al. |
| 6,723,044 B2 | 4/2004 | Pulford et al. |
| 6,814,078 B2 | 11/2004 | Crook |
| 6,846,287 B2 | 1/2005 | Bonadio et al. |
| 6,866,861 B1 | 3/2005 | Luhman |
| 6,902,541 B2 | 6/2005 | McNally et al. |
| 6,908,430 B2 | 6/2005 | Caldwell et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 7,033,319 B2 | 4/2006 | Pulford et al. |

| | | | |
|---|---|---|---|
| 7,052,454 B2 | 5/2006 | Taylor | |
| 2001/0037053 A1 | 11/2001 | Bonadio et al. | |
| 2002/0002324 A1 | 1/2002 | McManus | |
| 2002/0038077 A1 | 3/2002 | de la Torre et al. | |
| 2002/0072762 A1 | 6/2002 | Bonadio et al. | |
| 2003/0040711 A1 | 2/2003 | Racenet et al. | |
| 2003/0187376 A1 | 10/2003 | Rambo | |
| 2003/0192553 A1 | 10/2003 | Rambo | |
| 2003/0225392 A1 | 12/2003 | McMichael et al. | |
| 2004/0015185 A1 | 1/2004 | Ewers et al. | |
| 2004/0024363 A1 | 2/2004 | Goldberg | |
| 2004/0049099 A1 | 3/2004 | Ewers et al. | |
| 2004/0049100 A1 | 3/2004 | Butler et al. | |
| 2004/0054353 A1 | 3/2004 | Taylor | |
| 2004/0073090 A1 | 4/2004 | Butler et al. | |
| 2004/0092796 A1 | 5/2004 | Butler et al. | |
| 2004/0106942 A1 | 6/2004 | Taylor et al. | |
| 2004/0127772 A1 | 7/2004 | Ewers et al. | |
| 2004/0154624 A1 | 8/2004 | Bonadio et al. | |
| 2004/0267096 A1 | 12/2004 | Caldwell et al. | |
| 2005/0020884 A1 | 1/2005 | Hart et al. | |
| 2005/0059865 A1 | 3/2005 | Kahle et al. | |
| 2005/0222582 A1 | 10/2005 | Wenchell | |
| 2005/0241647 A1 | 11/2005 | Nguyen et al. | |
| 2005/0267419 A1 | 12/2005 | Smith | |
| 2005/0288558 A1 | 12/2005 | Ewers et al. | |
| 2006/0030755 A1 | 2/2006 | Ewers et al. | |
| 2006/0084842 A1 | 4/2006 | Hart et al. | |
| 2006/0129165 A1 | 6/2006 | Edoga et al. | |
| 2006/0149306 A1 | 7/2006 | Hart et al. | |

FOREIGN PATENT DOCUMENTS

| | | |
|---|---|---|
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S960196 | 8/1997 |
| IE | S970810 | 11/1997 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 11-290327 | 10/1999 |
| JP | 2002-28163 | 1/2002 |
| JP | 02003 235879 A | 8/2003 |
| WO | WO95/07056 | 3/1995 |
| WO | WO95/22289 | 8/1995 |
| WO | WO 95/24864 | 9/1995 |
| WO | WO 95/27468 | 10/1995 |
| WO | WO 99/15068 | 4/1999 |
| WO | WO 99/25268 | 5/1999 |
| WO | WO 00/32116 | 6/2000 |
| WO | WO00/54677 | 9/2000 |
| WO | WO0054675 | 9/2000 |
| WO | WO01/08581 | 2/2001 |
| WO | WO 2004/075730 A2 | 9/2004 |
| WO | WO 2004/075730 A3 | 9/2004 |
| WO | WO 2004/075741 A2 | 9/2004 |
| WO | WO 2004/075741 A3 | 9/2004 |
| WO | WO 2004/075930 A2 | 9/2004 |
| WO | WO 2004/075930 A3 | 9/2004 |
| WO | WO 2005/034766 | 4/2005 |

OTHER PUBLICATIONS

Horigane, et al , Silicone Rumen Cannula with a Soft Cylindrical Part and a Hard Flange, Journal of Dairy Science, Nov. 1989, vol. 72, No. 11, pp. 3230-3232.

McSweeney, Cannullation of the Rumen in Cattle and Buffaloes, Australian Veterinary Journal, Aug. 1989, vol. 66, No. 8, pp. 266-268.

Yamazaki et al., Diurnal Changes in the Composition of Abomasal Digesta in Fasted and Fed Sheep, The Tohoku Journal of Argricultural Research, Mar. 1987, vol. 37, No. 3-4, pp. 49-58.

Neil Sheehan, Supplemental Expert Report of Neil Sheeham, Re: U S. Patent No. 5,741,298, United States District Court for the Central District of California, Civil Action No. SACV 03-1322 JVS Aug. 9, 2005.

European Patent Office, Supplementary European Search Report for European Application No. EP 01 97 3379, dated Jul. 5, 2007, based on International Patent Application No. PCT/US01/29682, filed Sep. 21, 2001.

WOUND RETRACTION APPARATUS AND METHOD

CROSS-REFERENCE TO RELATED APPLICATIONS

This application is a continuation of U.S patent application Ser. No. 11/218,412, filed on Sep. 1, 2005, now U.S. Pat. No. 7,238,154, which is a continuation of U.S. patent application Ser. No. 10/399,209, filed on Aug. 22, 2003, now U.S. Pat. No. 6,958,037, which claims benefit of PCT application serial no. PCT/US01/50742, filed on Oct. 20, 2001, and entitled "Wound Retraction Apparatus and Method," the disclosures of which are hereby incorporated by reference as if set forth in full herein.

CROSS REFERENCE TO RELATED APPLICATIONS

This is a non-provisional application claiming the priority of provisional application Ser. No. 60/241,953 filed on Oct. 19, 2000, entitled "Hand-Assisted Laparoscopy Apparatus and Method", as well as the PCT application Ser. no. PCT/US01/29682, filed on Sep. 21, 2001, and entitled "Surgical Access Apparatus and Method," both of which are fully incorporated herein by reference.

BACKGROUND OF THE INVENTION

1. Field of Invention

This invention relates generally to wound retraction and more specifically to wound retraction in a laparoscopic surgical procedure.

2. Discussion of the Related Art

During laparoscopic surgery, it is desirable to inflate the abdominal cavity in order to increase the volume of the working space. This is accomplished with an insufflation gas which must be maintained at a pressure sufficient to inflate the abdomen. Maintaining the pressure of the insufflation gas is difficult when it is also desirable to insert instrumentation through the abdominal wall. If the surgeon is interested in inserting his or her hand in a hand-assisted laparoscopic procedure, the maintenance of insufflation pressure is even more difficult. Currently, several devices exist that accomplish this surgical need although they suffer from drawbacks such as difficult placement and cumbersome use. Thus, it is desirable that the wound be retracted, protected, and fixed while maintaining an insufflation seal.

SUMMARY OF THE INVENTION

Wound retraction in accordance with the present invention allows the surgeon to easily locate a retractor and to provide a solid base for an instrument or hand seal. This retractor removes the tissue pressure from the wrist during hand-assisted laparoscopic surgery. It can also protect the tissue at the wound site, for example, from abrasion, bacteria or other contaminants organs, such as donor kidneys to be removed with minimal risk or damage. The retractor also opens the wound providing greater access to the operative site for instruments, such as the hand of the surgeon.

In one aspect of the invention, a surgical wound retractor is adapted to dilate a wound stretchable to a desired diameter. The retractor includes a first ring having a diameter greater than the desired diameter and being adapted for disposition interiorly of the wound. A second ring having a diameter greater than the desired diameter of the wound is adapted for disposition exteriorly of the wound. A plurality of retraction elements are disposed in a generally cylindrical relationship to each other, between the first ring and the second ring. The retraction elements are adapted for disposition through the wound to exert a radial retraction force on the wound, the retraction force being dependent on the distance separating the first ring and the second ring.

In another aspect of the invention, the surgical wound retractor concludes a plurality of retraction elements each having a distal end and a proximal end, the distal end being coupled to the first ring. The retraction elements have a plurality of engagement sites disposed between the proximal end and the distal end, each of the engagement sites being associated with a different retraction force. The second ring has properties for engaging a selected one of the engagement sites to provide the desired radial retraction force. The engagement sites may include a plurality of ladder rungs, detents or enlargements, each associated with a different retraction force.

The wound retractor may include a retraction sleeve with a first end coupled to the first ring and a second end coupled to the second ring. A third ring carried by the sleeve between the first end and the second end is adapted for disposition exteriorly of the wound. The second ring and the third ring are provided with elastomeric properties facilitating circumferential rolling of the second ring relative to the third ring to provide the sleeve with a radial retraction force sufficient to stretch the wound to the desired diameter.

In a further aspect of the invention, the third ring is disposed circumferentially of the sleeve and moveable between a plurality of positions between the first ring and the second ring. Each of the positions is associated with a different radial retraction force. The retractor includes means for retaining the third ring at one of the plurality of positions to provide the desired radial retraction force associated with that position. This retention means may include a fourth ring adapted to fix the sheath between the third ring and the fourth ring at the desired position. The retention means may also include a clip providing the sheath and the third ring with a fixed relationship. A plurality of circumferential tubes may be included in the retention means, each of the tubes having a fixed relationship with the sheath at one of the desired positions. The tubes are sized and configured to receive alternatively the third ring at the associated position. Angular tracks can be included in the retention means with the ring configured to mount relative to one of the tracks at the associated position.

In a further aspect of the invention, a method for operating the surgical wound retractor includes the step of providing a retraction sleeve having an axis, a first end attached to a first ring and a second end attached to a second ring axially spaced from the first ring. A third ring is provided in a generally fixed relationship to the sleeve between the first ring and the second ring. Then the second ring and third ring are circumferentially rolled to form a circumferential retainer positioned axially of the first ring at a particular distance associated with the desired radial retraction force on the wound. In the rolling step, the third ring can be rolled outwardly of the second ring to form the circumferential retainer. The second ring can then be rolled outwardly of the third ring to move the circumferential retainer to the particular distance.

These and other features and advantageous of the invention will become more apparent with a description of preferred embodiments and reference to the associated drawings.

DESCRIPTION OF THE DRAWINGS

FIG. 12-FIG. 15 are axial perspective views showing steps in a preferred method for operating the FIG. 10 embodiment;

DESCRIPTION OF PREFERRED EMBODIMENTS AND BEST MODE OF THE INVENTION

Figure 1:
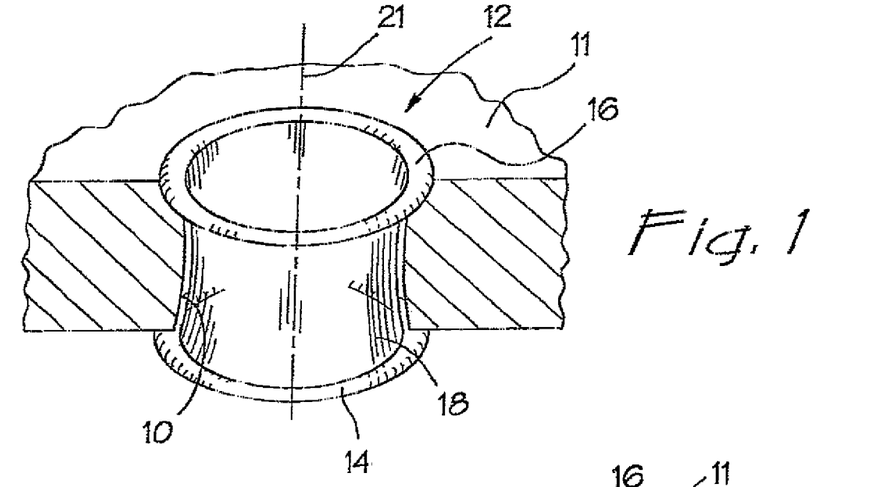
FIG. 1 is a perspective view of one embodiment of the present invention.

The basic concept of retracting and protecting a wound site is illustrated in the prospective view of FIG. 1 wherein a wound 10 is formed in an abdominal wall 11. In this embodiment, a retractor 12 uses two rings 14 and 16 which are fixed to an elastic sheath 18. The sheath 18 has a generally cylindrical configuration and is disposed along an axis 21. The rings 14 and 16 are disposed in respective planes which extend radially of the axis 21.

The sheath 18 has elastomeric properties, but in its natural, unstretched state the two rings 14 and 16 are separate by a natural distance. The lower ring 14 is placed interiorly of the abdominal wall 11 and the upper ring 14 is stretched beyond the natural distance away from the lower ring. Once the elastic sheath 18 has been stretched to a distance greater than the abdominal wall thickness, the upper ring 16 is placed on the surface of the skin.

Since the diameters of the rings 14, 16 are greater than that desired for the wound site 10, they will have sufficient footing to maintain this tension between the two rings 14, 16. This tension is created by the elastic material that has been stretched and retained at a distance greater than the natural distance. It will be appreciated that in many embodiments, the sheath 18 can be formed of a non-elastic sheathing material. In a similar manner, the rings 14 and 16 may be provided with a rigid configuration or alternatively may be formed of an elastromeric material.

Figure 2:
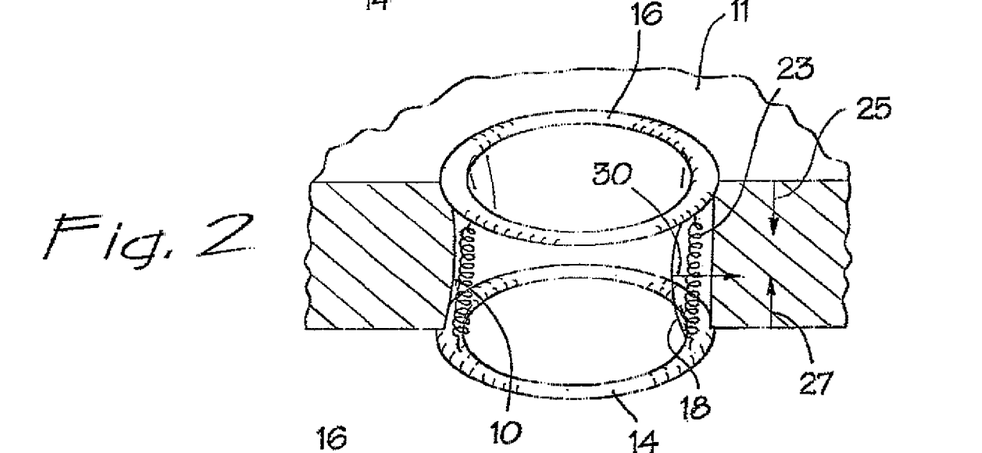
FIG. 2 is a perspective axial cross section view of the embodiment illustrated in FIG. 1.

FIG. 2 shows a simple schematic of the ring dynamics illustrated in FIG. 1, with the retractor 12 operatively disposed across the abdominal wall 11. The elastic sheet sheath 18 acts as a circumferential spring 23 around the wound site 10 that evenly distributes the tension between the two rings 14 and 16, as represented by arrows 25 & 27. In addition, the elastic sheeting provides a radial retraction force 30 around the wound to enlarge the wound site 10 in order to facilitate the passage of instruments, such as the hand of the surgeon.

The amount of tension force between the two rings 14 and 16 can be controlled by the elastomeric proportion of the elastic sheath 18. In order to accommodate a larger range of abdominal wall thicknesses, a material with a higher elasticity can be chosen to allow for greater stretch.

Figure 3:
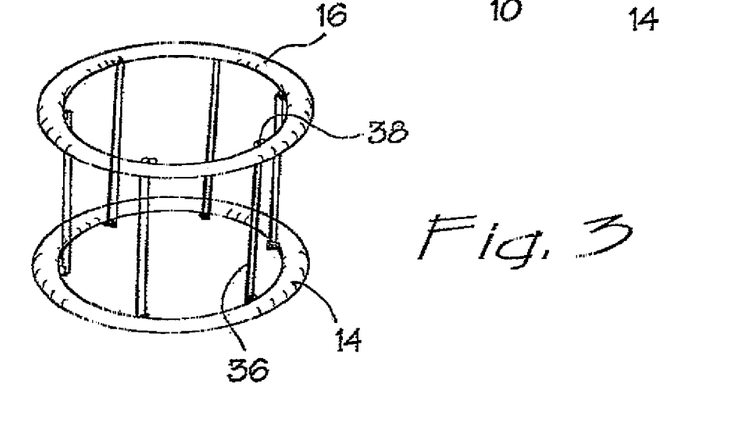
FIG. 3 is a perspective view of an additional embodiment of the invention including multiple retraction elements.

FIG. 3 illustrates the "sandwiching" of the abdominal wall between the two rings 14, 16 using elastic tensioners, such as rubber bands 36. The use of elastic tensioners allows for a greater range of wall thicknesses because the tensions can be selected at the time of application. For instance, the user would make an incision and measure the actual abdominal wall thickness. He would then choose the appropriate rubber bands providing the desired tensions for the given application. In this case the rubber bands 36 could be secured by hooks 38 provided on one or both of the rings 14 and 16. This gives the user more versatility with the device.

Figure 4:
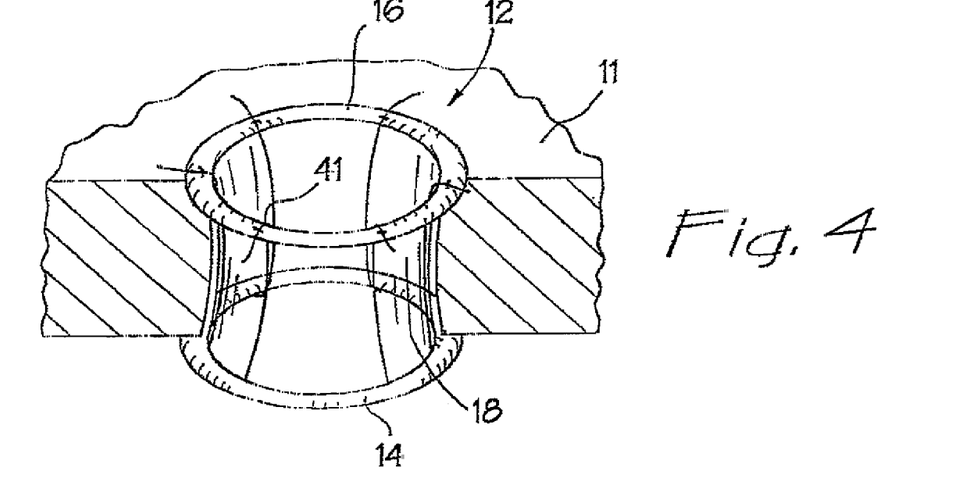
FIG. 4 is a perspective view of an additional embodiment of the invention including an elastomeric sleeve and multiple retention elements secured onto hook features.

FIG. 4 is a different embodiment which provides even further versatility. This design is not limited by the fixed distance between the rings 14, 16 of the retractor 12. Instead, the inner ring 14 will be fixed to the sheath 18, and the upper ring 16 will comprise a separate assembly. Initially, the inner ring 14 is placed into the peritoneum cavity. Then the elastic material is pulled taut and secured onto hook features 41 located on the outer ring 16. This allows the user to fix the retractor 12 to an abdominal wall of any size.

Figure 5:
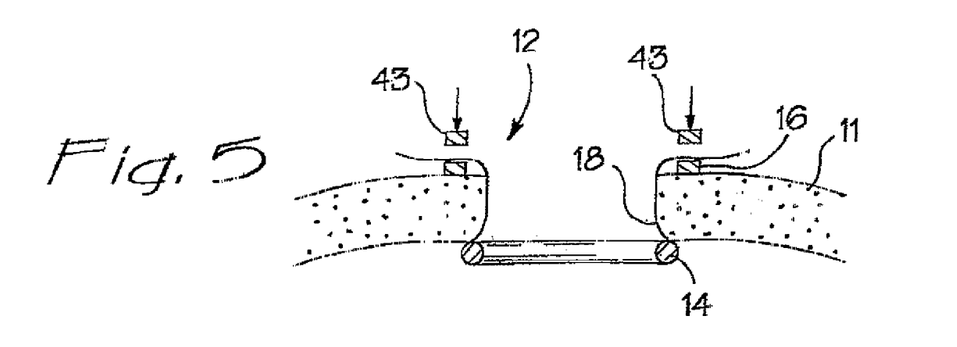
FIG. 5 having a sheath attached to an outer ring with clamps.
Figure 6:
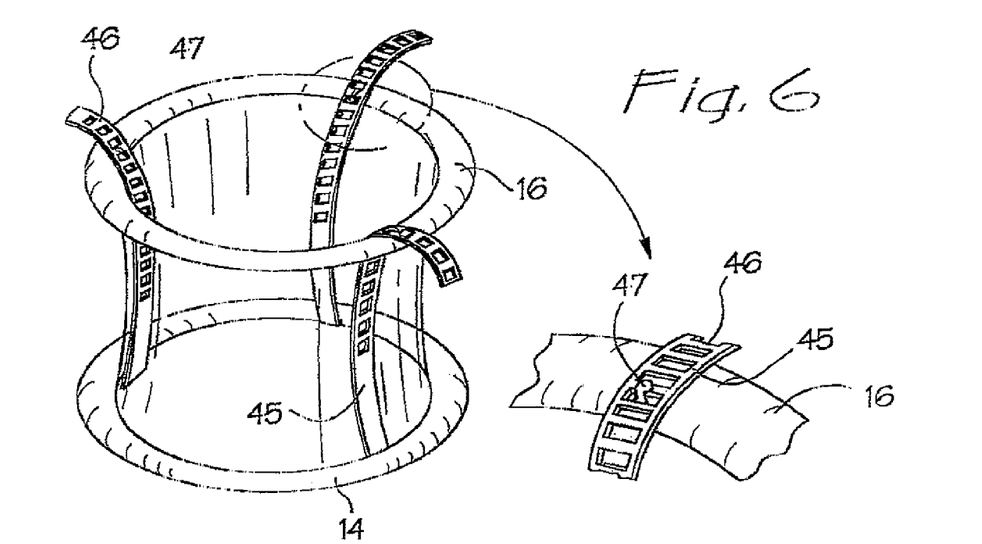
FIG. 6 is a perspective view of a further embodiment of the invention including multiple ladders with rungs providing a sheath with desired tension.

FIG. 5 shows an additional embodiment wherein the sheath 18 is attached to the outer ring 16 using clamps 43. FIG. 6 illustrates another embodiment wherein the sheath 18 is attached to the outer ring 16 using ladders 45 with rungs 46, that may be connected to the external surface of the sheath 18. Once the preferred tension of the sheath 18 has been attained, the user simply hooks an appropriate rung 46 onto an associated hook 47 located on the outer ring 16.

Figures 7A, 7B:
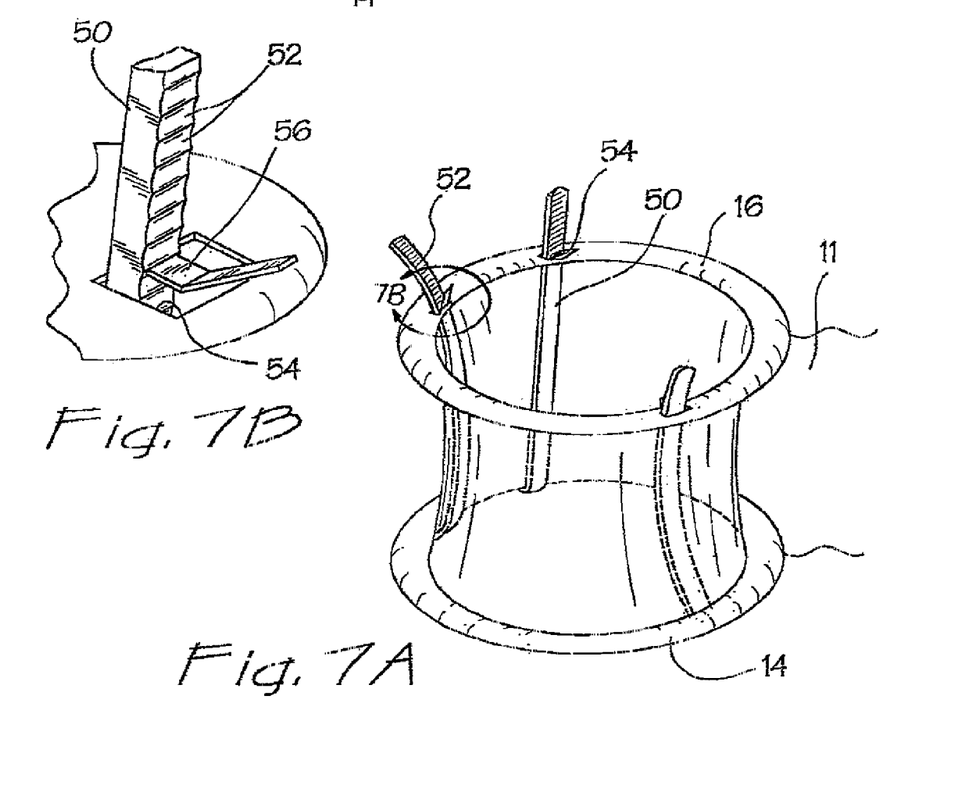
FIG. 7A is a perspective view of a further embodiment of the invention including retention elements in the form of zip ties with detents.
FIG. 7B is an enlarged perspective view of a detent adapted for use in the embodiment of FIG. 7A.

FIG. 7A shows a structure which sandwiches the abdominal wall 11 between the two rings 14, 16 using zip ties 50. After the inner ring 14 has been placed, the ties 50 can be pulled tight through associated holes 54 to fix the rings 14, 16 relative to the abdominal wall 11. As illustrated in FIG. 7B, the zip ties 50 may be formed with a plurality of grooves 52 which extend traverse or perpendicular to the length of the tie 50. In operation, the tie 50 is threaded through the hole 54 in the upper ring 16 where one of the grooves 52 is engaged by a tongue 56 which prevents movement of the tie 50 back through the hole 54.

Figures 8A, 8B, 10:
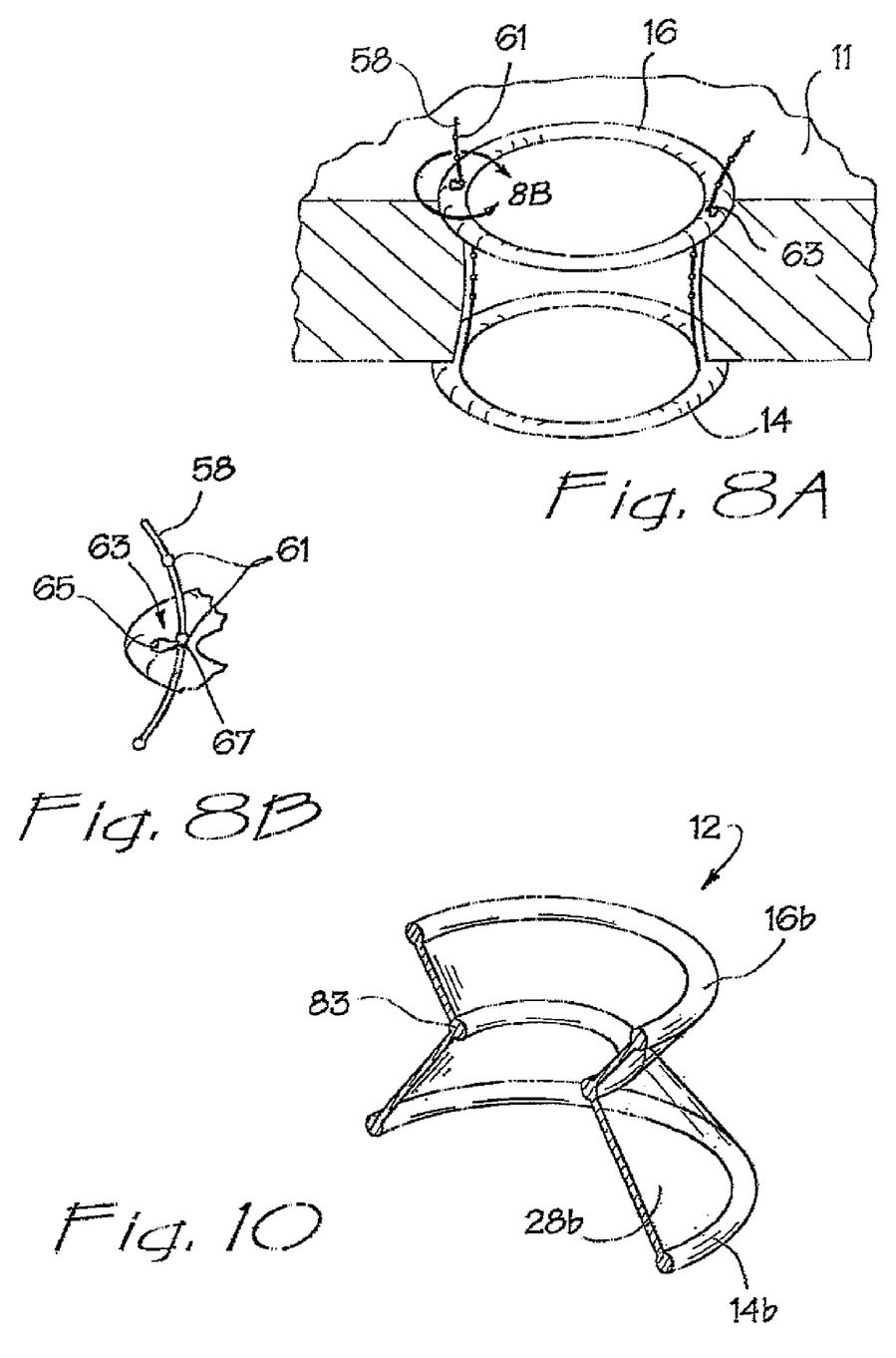
FIG. 8A is a perspective view of an additional embodiment of the invention wherein the retention elements include a series of ropes with enlargements or knots operable relative to a window in the outer ring.
FIG. 8B is an enlarged perspective view of a window configuration adapted for use with the embodiment of FIG. 8A.
FIG. 10 is an axial perspective view of a further embodiment including a moveable third ring.

FIG. 8A shows a method of sandwiching the abdominal wall between the two rings 14, 16 using a series of ropes 58, each having a plurality of knots 61. After the ring 14 has been placed, the ropes 52 can be tensioned and one of the knots 61 secured into an associated holder located on the outer ring 16. In this embodiment, each rope 58 is drawn upwardly through an associated window 63 in the outer ring 16. This window 63 will typically be provided with portion 65 larger than the knots 61, and portion 67 smaller than the knots 61 as illustrated in FIG. 8B.

Figure 9:
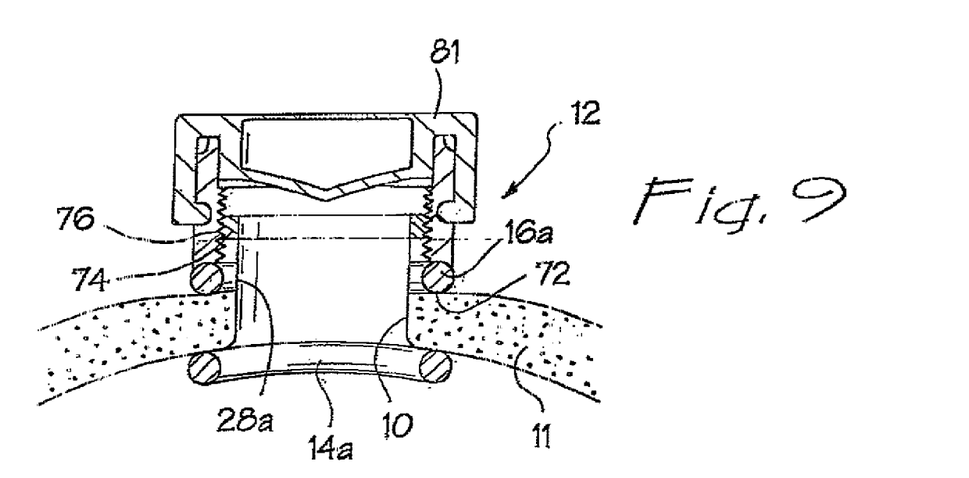
FIG. 9 is an axial cross section view of a further embodiment of the invention including a threaded second ring and a threaded third ring operable with a sealing cap.

An additional embodiment of the wound retractor 12 is illustrated in FIG. 9 where elements of structure similar to those previously described are designated by the same reference numeral followed by the lower case letter "a."

This embodiment is adapted for opening the wound 10 in the abdominal wall 11 and for maintaining the wound 10 in the open configuration to allow access into the abdominal cavity The device includes the sheath 28a which lines the wound 10 to prevent or limit the risk of portsite metastasis, and the outer ring 16a which has internal threads 70. The outer ring 16a also includes a sealing surface 72 at its base which is designed to seal against the exterior surface of the abdominal wall 11. The device further comprises the thin film sheath 28a with a ring 74, having external threads 76, which is attached to the proximal end of the sheath 28a, and with the inner ring 14a attached to the distal end of the sheath 28a. The inner ring 14a is designed to be placed inside the wound 10 while the rings 16a and 74 remains external to the wound 10.

Once the inner ring 14a is placed inside the wound 10 and into the peritoneal cavity, the outer ring 16a can be rotated clockwise relative to the inner ring 14a. As the internal thread 70 on the outer ring 16a engage the external threads 76 on the ring 74, the ring 74 is drawn proximally stretching the sheath 28a. This opens the wound 10 and draws both the outer ring 16a and the inner ring 14a toward the abdominal wall 11. A primary seal is created between the inner ring 14a and the abdominal wall 11, while a secondary seal is formed between the surface 72 of the outer ring 16a and the exterior surface of the abdominal wall 11. A sealing cap 81 can then be attached to the proximal end of the outer ring 16a to permit insufflation and otherwise facilitate a laparoscopic procedure. The sealing cap 81 can be removed at any time to allow conversion from laparoscopic surgery to open surgery.

Perhaps the most significant advantage associated with this embodiment is that the device enables a surgeon to retract and protectively line an abdominal wall incision, while being able to easily adjust the retractor 12a to accommodate variations from patient to patient in the thickness of the abdominal wall 11. The device effectively seals around the interior and exterior of the wound 10, which allows the sealing cap 81 to be attached to seal the abdominal cavity and enable a laparoscopic procedure to be performed.

Another embodiment of the retractor 12 is illustrated in FIGS. 10-14 where elements of structure similar to those previously discussed are designated with the same reference numeral followed by the lower case letter "b." In this embodiment, the retractor 12b includes the thin film sheath 28b which lines the wound to prevent or limit the risk of portsite metastasis. The inner and outer rings, 14b and 16b, respectively, are attached to opposing ends of the sheath 28b in the manner previously described. However, in this embodiment, a third ring 83 is fixed to the sheath 28b between the rings 14b and 16b.

Figure 11A:
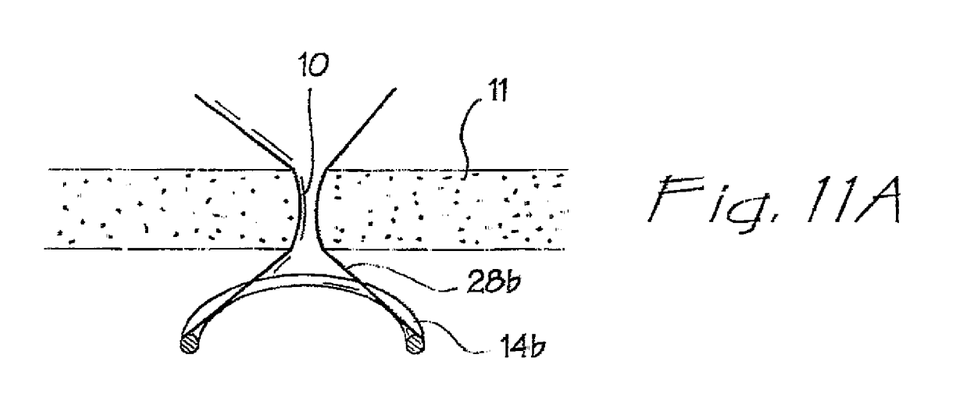
FIG. 11A is an axial schematic view showing the FIG. 10 embodiment in a natural state.
Figure 11B:
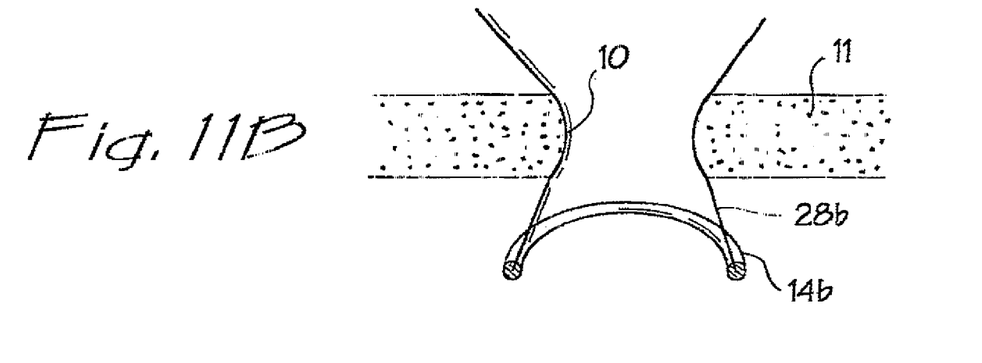
FIG. 11B is an axial schematic view showing the FIG. 10 embodiment in a retraction state.

In order to achieve the desired retraction, the inner ring 14b is positioned interiorly of the abdominal wall 11 as illustrated in FIG. 11A. Then the sheath 28b is pulled outwardly through the wound 10, tensioning the sheath 28b and causing the abdominal wall 11 to retract or open as illustrated in FIG. 11B.

At this point, it is desirable to maintain the retraction by preventing the sheath 28b from pulling back into the wound 10. This maintenance of tension on the sheath 28b is addressed in a unique manner with the embodiment of FIG. 10 wherein the rings 16b and 83 are preferably provided with elastromeric characteristics.

Figure 12:
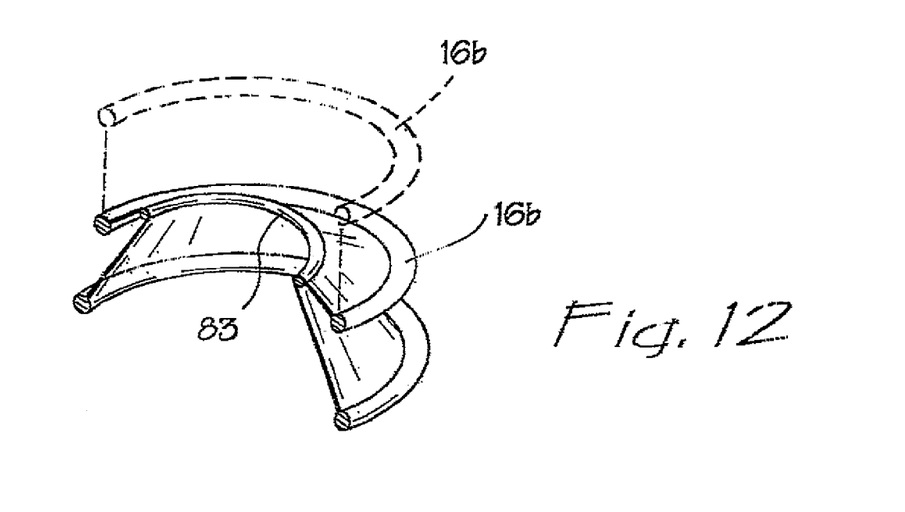
FIG. 12 is an axial perspective view showing the second ring being rolled over the third ring to create a circumferential retainer.
Figure 13:
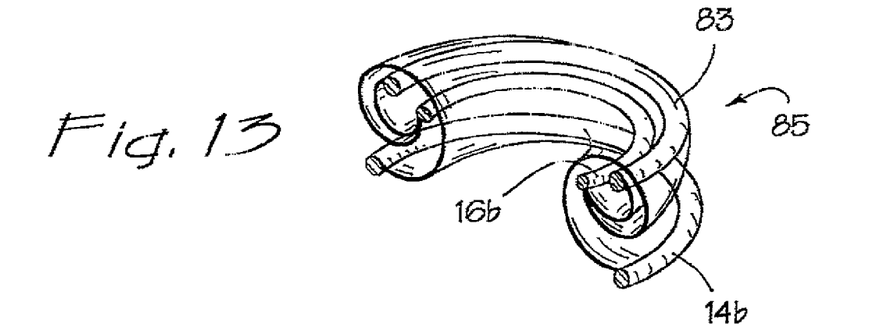
FIG. 13 is an axial perspective view showing the third ring being rolled over the second ring to move the circumferential retainer to a desired position.
Figure 14:
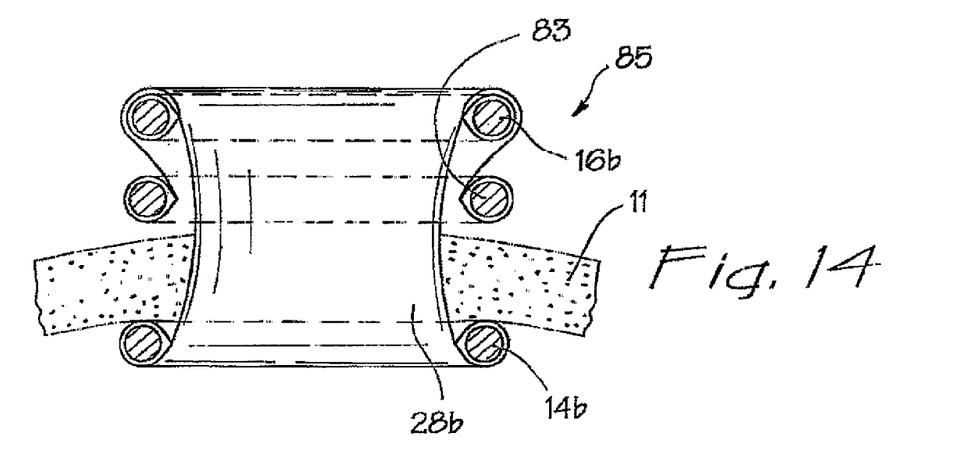
FIG. 14 is an axial view showing the step of FIG. 12 with the retractor operatively disposed.

In the manner illustrated in FIG. 12, the ring 16b can be moved distally over the ring 83. This creates a circumferential retainer or ring bundle 85 which is illustrated in the perspective view of FIG. 13. In this process, the ring 16b is stretched circumferentially outwardly of the ring 83 to form the bundle 85. This formation is further illustrated in the cross section schematic view of FIG. 14 where the bundle 85 of elastomeric rings presses against the outer surface of the abdominal wall 11 to maintain tension on the sleeve 28b.

Figure 15:
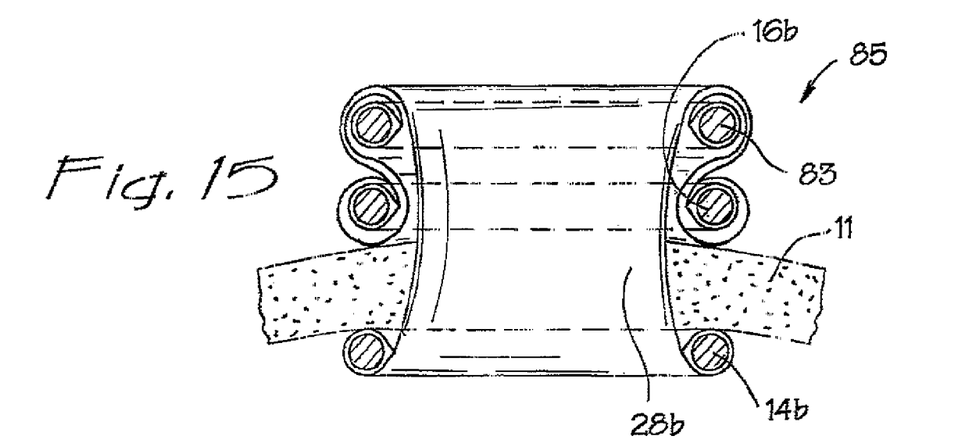
FIG. 15 is an axial cross section view of the step illustrated in FIG. 13 showing the retractor operatively disposed.

With reference to FIG. 15, it will be appreciated that the ring bundle 85 can be further rotated to move the third ring 83 outwardly and distally of the ring 16b as required to produce and maintain the desired tension on the sheath 28b.

With the embodiment of FIG. 10, retraction is achieved by positioning the ring 83 above the ring 16b, and pulling the sheath 28b upwardly from the wound 10 (FIG. 12). The sheath is prevented from pulling back into the incision by stretching the ring 83 out, around, and under the ring 16b.

The degree of retraction or how much the sheath is pulled upwardly, is depended on the height of the ring 83 about the abdominal wall 11. This height can be adjusted in the embodiment of FIG. 16 wherein elements of structure similar to those previously described are designated with the same reference numeral followed by the lower case letter "c." In this embodiment, the ring 83c can be disconnected from and moved relative to the sheath 28c. At a desired location above the inner ring 14c, the ring 83c can be fixed to the sheath 28c, for example by a clip 87.

Figure 16:
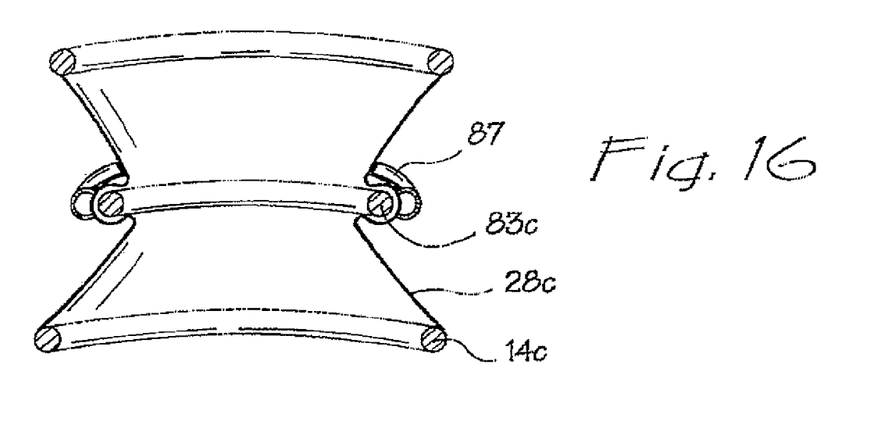
FIG. 16 is an axial perspective view of a further embodiment including a clip for retaining the third ring at a desired position between the second ring and the first ring.
Figure 17:
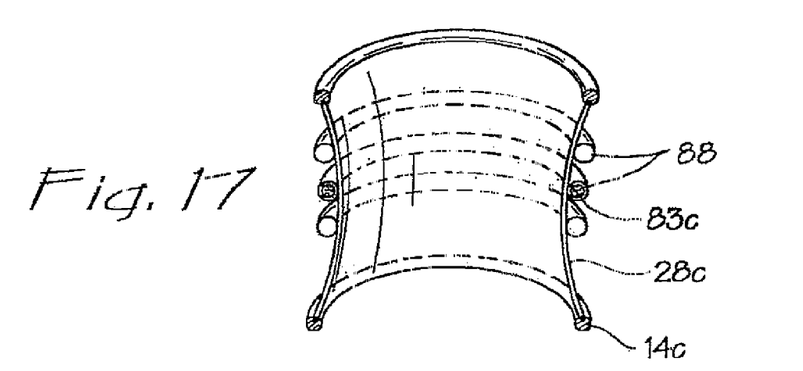
FIG. 17 is an axial perspective view showing multiple loops each disposed at a particular distance from the first ring and adapted to alternatively receive the third ring at a desired distance from the first ring.
Figure 18:
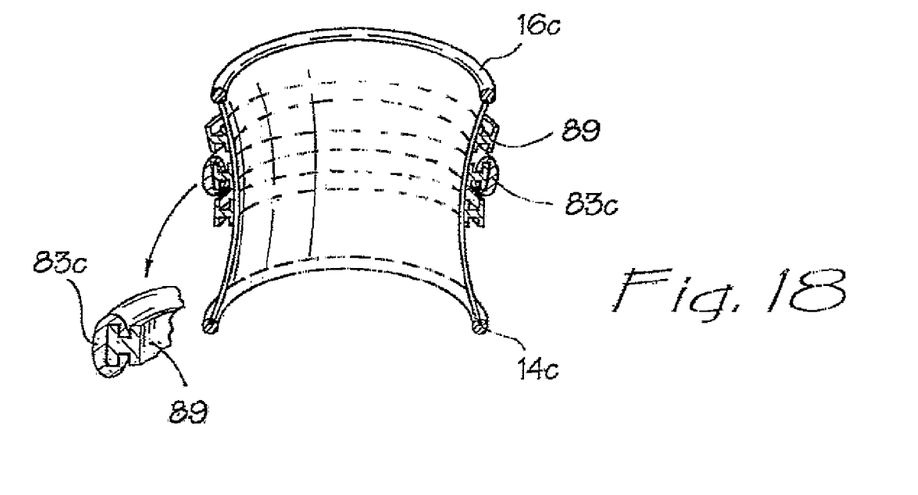
FIG. 18 is an axial perspective view of an embodiment including tracks and a third ring with a mating groove.

Clamps or clips may be used to lock the movable ring at the appropriate height as shown in FIG. 16. Also, a series of open loops 88 (FIG. 17) or tracks 89 (FIG. 18) can be fixed to the sheath 28c at different distances from the inner ring 14c to hold the ring 83c at different heights.

Figure 19:
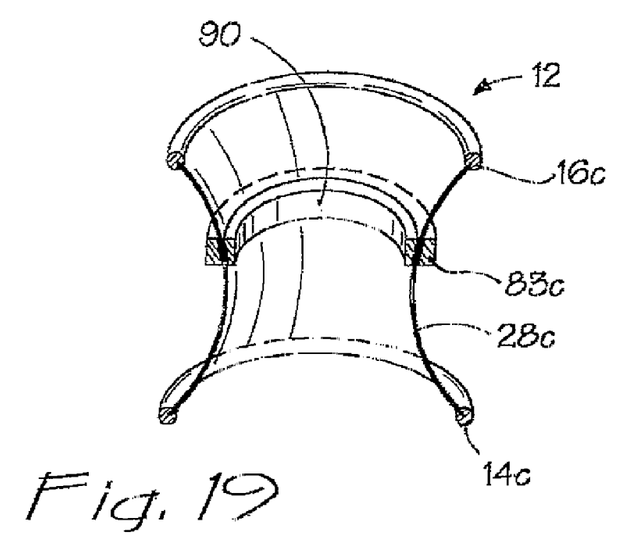
FIG. 19 is an axial perspective view of an embodiment including a fourth ring for clamping the sheath between the third ring and the fourth ring.

Alternatively, as illustrated in FIG. 19, the moveable ring 83 can be formed as two complimentary rings. The outer ring 16b can be disposed outwardly of the sheath 28c and a fourth ring 90 can be disposed inwardly of the sheath 28c. These two rings 14c and 90 function to clamp the sheath 28c so that the ring 83c is maintained in a fixed position by the complimentary locking ring 90.

The inner locking rings 83c and 90 of the FIG. 19 embodiment provide for simple operation of the retractor 12. These interlocking rings 83 and 90 can be pushed down so that they rest on the outer surface of the abdominal wall 11. As the sheath 28c is drawn upwardly to achieve the proper degree of tension, it is easily moved between the rings 83c and 90 However, any tendency of this sheath 28c to move back into the wound site merely tightens the interlocking relationship of the rings 83c and 90. Thus, the desired degree of tension is maintained on the sheath 28c until it is again pulled to release the locking ring 90 from the ring 83c.

Figure 20:
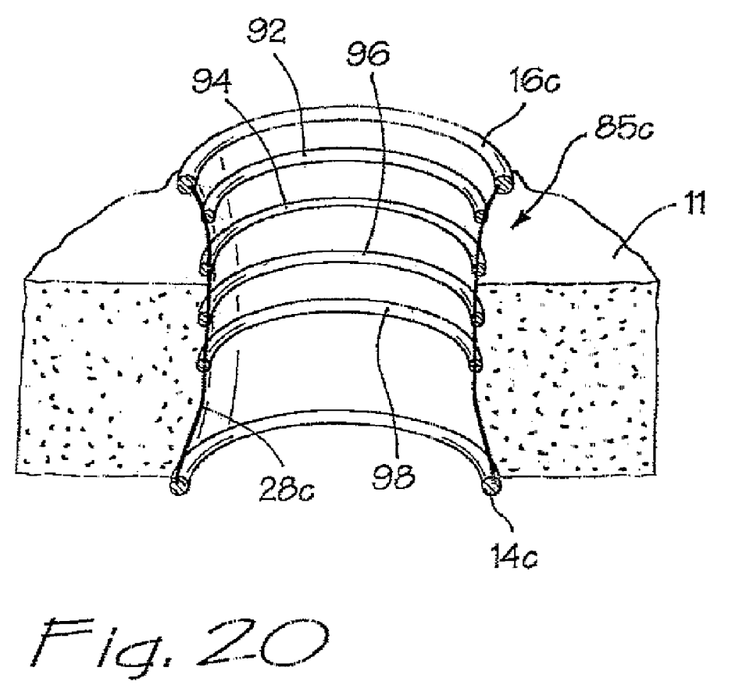
FIG. 20 is an axial perspective view of a further embodiment including a series of third rings for forming the retention roll at different positions between the first and second rings.

In still a further embodiment, illustrated in FIG. 20, several intermediate rings, 92, 94, 96 and 98 can be provided between the inner ring 14c and the outer ring 16c. With this embodiment, the rings, such as the ring 16c, 92 and 94, disposed outwardly of the abdominal wall 11 can be rolled into the ring bundle 85c to maintain the desired tension on the sheath 28c. In this case, the rings 96 and 98, which are not included in the ring bundle 85c, contact the abdominal wall 11 to provide increased friction and perhaps increased retraction at the wound site.

A further advantage of these embodiments is that they enable the surgeon to retract and protectively cover the wound 10 while permitting adjustment of the retractor 12c to variations in thickness of the abdominal wall 11. These devices provide an airtight seal around the wound 10, thus allowing an airtight cap or access port to be attached to enable laparoscopic surgery. Furthermore, usage of these devices is simple in that retraction can be achieved with one motion by grasping the proximal ring 16c and pulling it up from the wound 10 and then merely releasing it.

Figure 21:
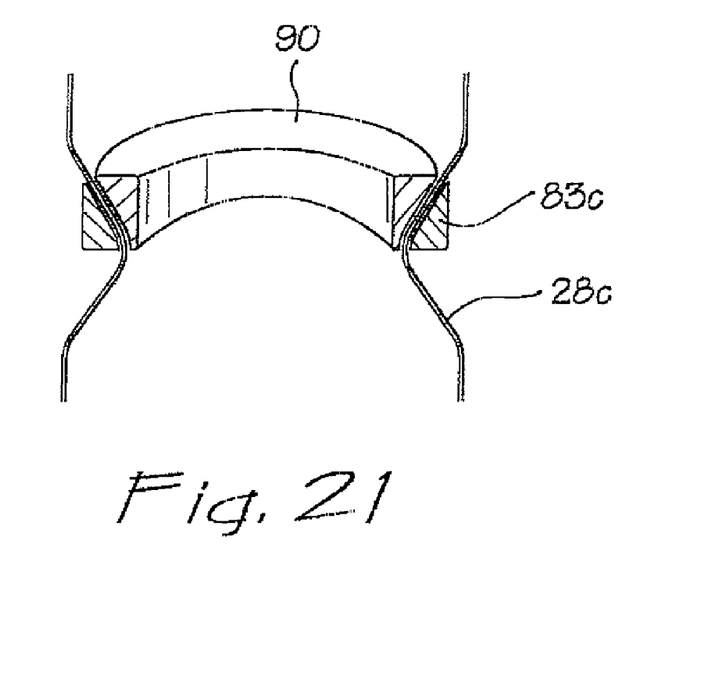
FIG. 21 is an axial perspective view of an embodiment including unidirectional interlocking rings in a separated state.
Figure 22:
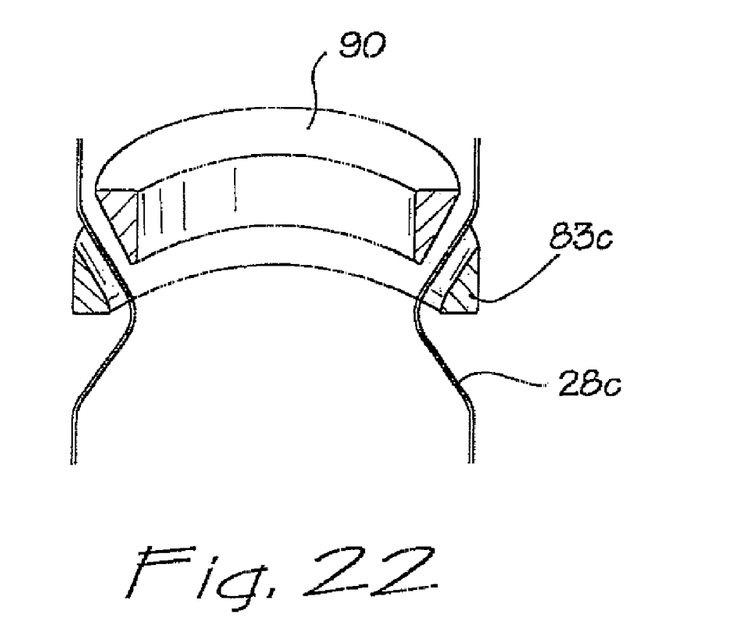
FIG. 22 is an axial perspective view of the unidirectional interlocking rings in a proximate clamping state.

The one-way characteristics of the interlocking rings 83c and 90 are illustrated in the progressive views of FIGS. 21 and 22. With reference to these figures, it can be seen that retraction is maintained by preventing the sheath 28c from pulling back into the wound 10 by means of the one-way operation of the interlocking rings 83c and 90. The sheath 28c slides easily through the interlocking rings 83c and 90 in the upper direction, but is prevented from sliding through the rings 83c and 90 in the downward direction. In order to disengage or separate the interlocking rings 83c and 90, one need only re-tension the sheath 28c by pulling it proximally thereby unlocking the rings 83c and 90. This enables the ring 83c to be removed from the sheath 28c in order to remove the retractor 12 from the wound site.

Figure 23A:
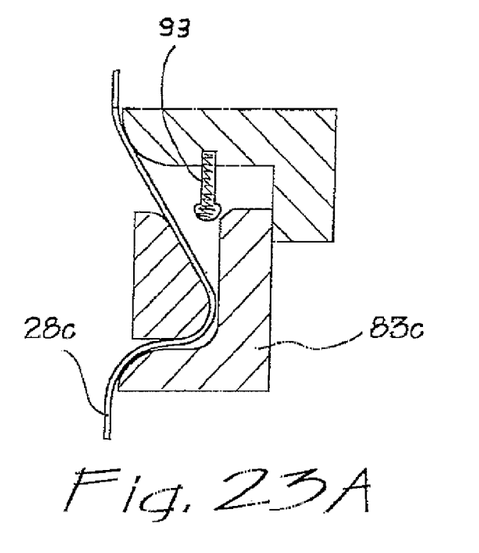
FIG. 23A is a cross sectional view showing a unidirectional mechanism with a third ring, fourth ring, and associated cap ring including a wedge.
Figure 23B:
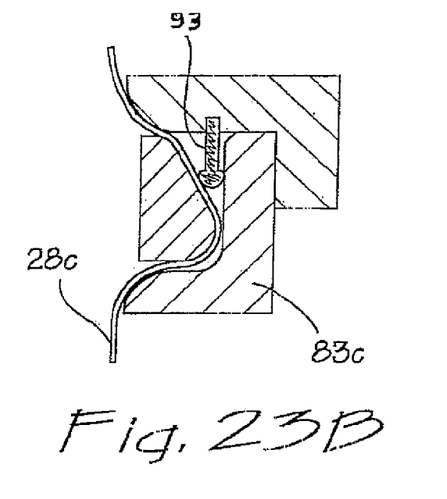
FIG. 23B shows the rings of FIG. 23A operatively disposed to wedge the sheath between the second and fourth rings.
Figure 24:
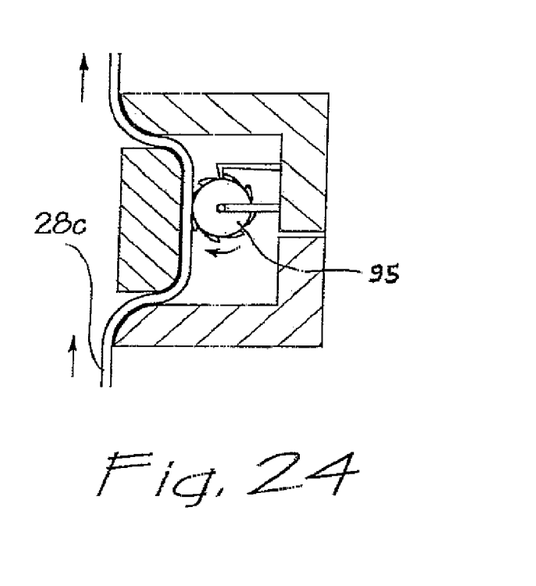
FIG. 24 is an axial cross section view showing an embodiment of a unidirectional retention member, including a one-way roller.
Figure 25:
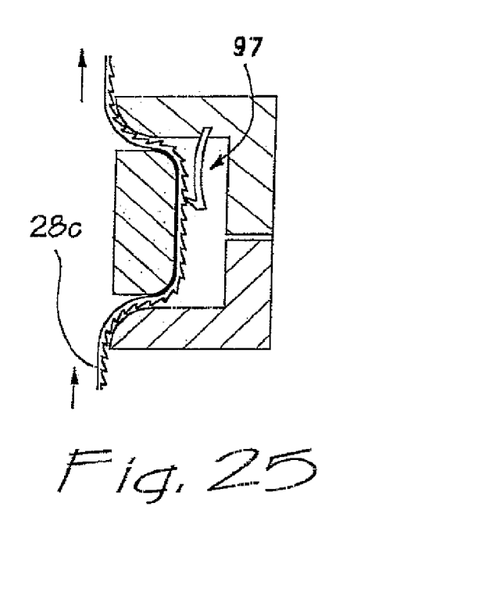
FIG. 25 is an axial cross section view showing a unidirectional retention member in the form of a ratchet.

Other one-way mechanisms can be formed, for example, with a wedge 92 as illustrated in FIGS. 23A and 23B, a one-way roller 94 as illustrated in FIG. 24, or a one-way ratchet 96 as illustrated in FIG. 25. Bumps, over-braid, threads or coatings on the sheath 28 can be added for additional traction using these one-way mechanisms. Alternatively, features such as indentations or protrusions on the sheath 28 can permit it to pass in only one direction.

Figure 26:
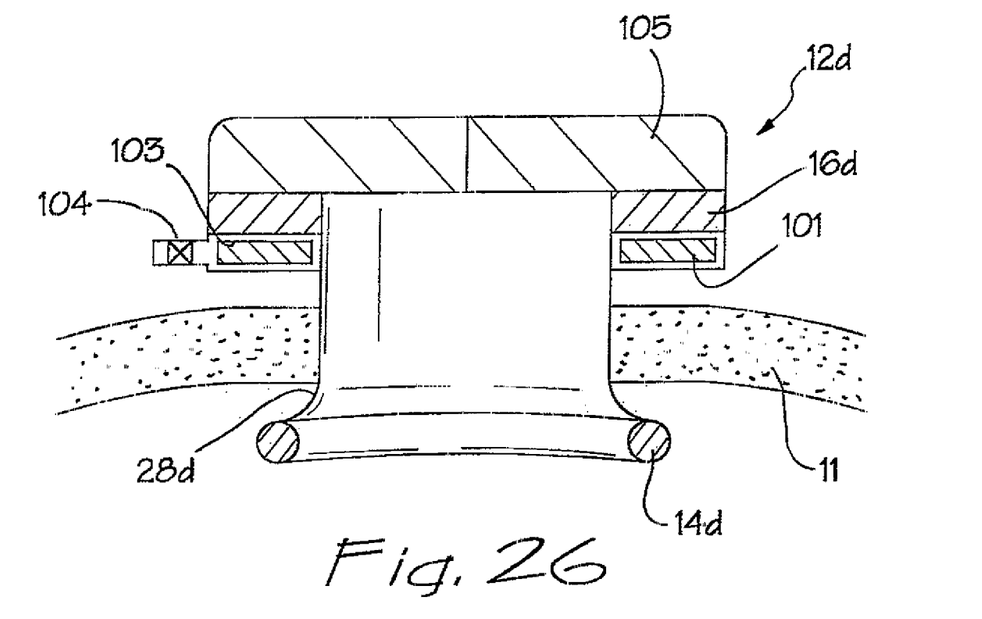
FIG. 26 is an axial cross section view of a further embodiment wherein the third ring is expandable to adjust the distance between the third ring and the first ring.
Figure 27:
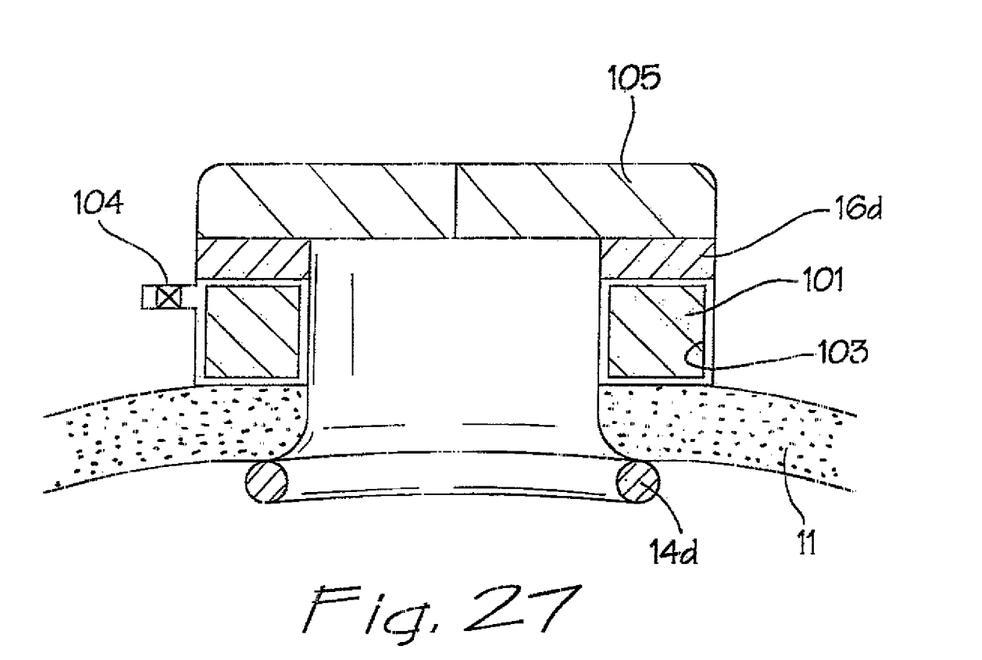
FIG. 27 is an axial cross section view showing the embodiment FIG. 26 with the third ring including foam in an expanded state.

A further embodiment of the wound retractor 12 is illustrated in FIGS. 26 and 27 wherein elements of structure are similar to those previously described or designated with the same reference numeral followed by the lower case letter "d." These embodiments include an expandable foam annulus 101 which is disposed in a compartment 103 sealed by a valve 104. This compartment 103 is formed between the rings 14d and 16d, and proximate the outer ring 16d. In this location, the compartment 103 is operatively disposed exteriorly of the abdominal wall 11. As in any of the embodiments previously disclosed, a sealing cap 105 can be disposed over the outer ring 16d to facilitate laparoscopic surgery. After the retractor 12d is operatively disposed as illustrated in FIG. 27. The valve 104 can be opened to permit air into the cavity 103. This also permits the foam annulus 101 to expand as illustrated in FIG. 27 thereby elevating the ring 16d above the abdominal wall 11 and tensioning the sheath 28d.

As the annular foam 101 expands to a high profile state, seals are formed on both sides of the wall 11 around the sheath 28d. In addition, the wall 11 is retracted from the wound 10. To remove the wound retractor 12 from the patient, the surgeon simply opens the valve 104 and pulls the inner ring 14d out through the wound 10. While an expandable foam is described for this embodiment, additional materials could be utilized which expand upon contact with the inlet air.

One advantage associated with this embodiment is that the device enables a surgeon to quickly retract and protectively line an abdominal wall incision while being able to easily accommodate variations from patient to patient in the thickness of the abdominal wall. In addition. The device effectively seals around the interior and exterior of the incision, and allows a sealing cap to be attached to seal the abdominal cavity and to enable a laparoscopic procedure to be performed.

Figure 28:
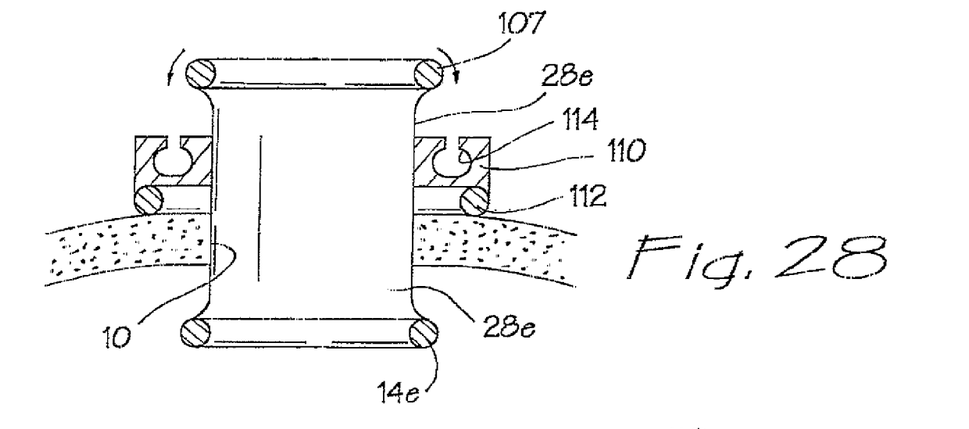
FIG. 28 is an axial cross section view of an embodiment showing a second ring being rolled into an inverted retention ring.
Figure 29:
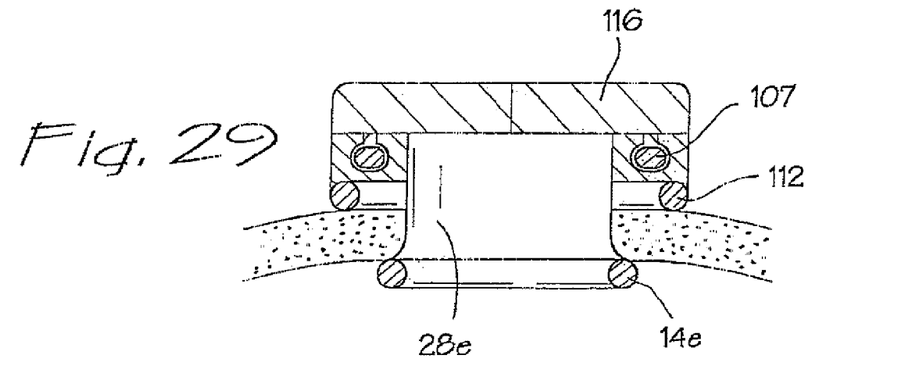
FIG. 29 is an axial cross section view showing the FIG. 28 embodiment with the rolled ring held by the retainer.

A wound retractor with an inverting ring 107 is illustrated in FIGS. 28 and 29 where elements of structure similar to those previously disclosed are designated with the same reference numeral followed by the lower case letter "e." The device includes the sheath 28e which lines the wound 10 to prevent or limit the risk of portsite metastasis. The device includes base 110 with a sealing ring 14 on its distal end, which is designed to seal against the exterior abdominal wall 11 of the patient. The device includes a thin film sheath 28e with the inverting ring 107 configured to lock into the base 110 which is attached to the proximal end of the sheath 28.

The sealing ring 14e is designed to be placed inside the incision while the external inverting ring 107 remains external to the incision. The base 110 is configured to move freely between the rings 14e and 107 Once the ring 14e is placed inside the incision and into the peritoneal cavity, the external ring 107 is continuously rolled or inverted, which draws the incision open and also draws both the external ring 107 and the peritoneal ring 14e toward the abdominal wall. Once all of the slack in the sheath 28e has been taken up by rolling or inverting the external ring 107, the external ring can then be pushed into a recess 14 in the base 110 which is configured to lock the ring in position and thereby maintain the tension on the sheath 28e. With the proper amount of tension placed upon the sheath 28e, a primary seal is created between the peritoneal ring 14e and the anterior abdominal wall, and a secondary seal is created between the sealing ring 112 of the base 110 and the exterior abdominal wall. A sealing cap 16 can then be attached to the proximal end of the base and the patient can be insufflated with carbon dioxide to allow a laparoscopic procedure such as a gastric bypass to be performed. The sealing cap can be removed at any time to allow conversion from laparoscopic surgery to open surgery.

A most significant advantage associated with this embodiment is that the device enables a surgeon to retract and protectively line an abdominal wall incision while being able to easily adjust the device to accommodate variations from patient to patient in the thickness of the abdominal wall. The device effectively seals around the interior and exterior of the incision, which allows a sealing cap to be attached to seal the abdominal cavity ad enable laparoscopic procedure to be performed.

Figure 30:
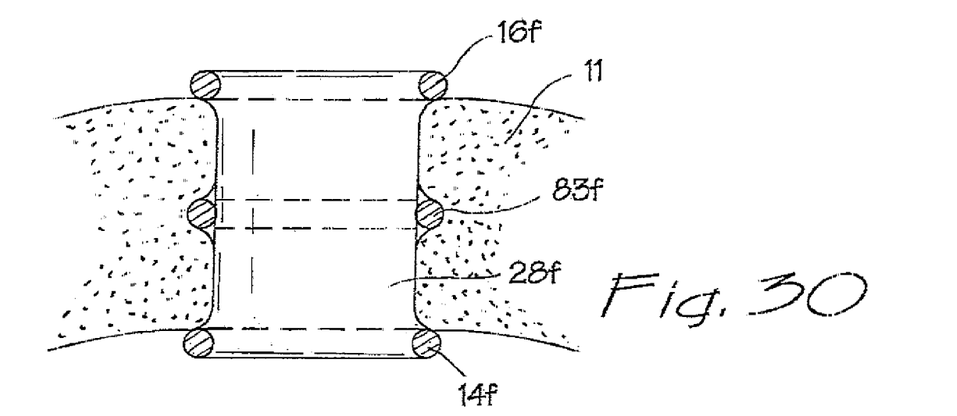
FIG. 30 is an axial cross section view illustrating an embodiment with two end rings and at least one intermediate ring.

A further embodiment of the wound retractor is, illustrated in FIG. 30, where elements of structure similar to those previously disclosed are designated with the same reference numeral followed by the lower case letter "f." This embodiment includes three separate rings 16f, 14f, and 83f. The device has a tubular sheath 28f which lines the incision to prevent or limit the risk of portsite metastasis. The device includes the external ring 16f attached to the proximal end of the sheath 28f, the intermediate ring 83f attached to the center of the sheath, and a peritoneal ring attached to the distal end of the sheath 28f. The peritoneal ring is designed to be placed inside the incision while the eternal ring 16f remains external to the incision. The intermediate ring 83f may remain external to the incision or may lie within the incision itself depending upon how the three rings are oriented.

This wound retractor has four different fixed lengths to accommodate abdominal walls of four different thicknesses. The first length, which is the longest, is achieved by simply placing the peritoneal ring 14f into the incision. The tension of the sheath between the external ring 16f and the peritoneal ring 14f maintains the incision in an open configuration. If the thickness of the abdominal wall 11 is less than the distance between the eternal ring 16f and the peritoneal ring 14f, then a shorter length can be selected.

The second length, which is less than the first length, is achieved by simply placing the peritoneal ring 14f into the incision, and then pulling the sheath 28f upwards until the intermediate ring 83f is external to the incision. The tension of the sheath 28f between the intermediate ring 83f and the peritoneal ring 14f maintains the incision in an open configuration. If the thickness of the abdominal wall 11 is less than the distance between the intermediate ring 83f and the peritoneal ring 14f then a shorter length can be selected.

The third length, which is less than the second length, is achieved by inserting the peritoneal ring 14f into the incision and then pulling the intermediate ring 83f over the external ring 16f. The tension of the sheath between the peritoneal ring and the combination of the external ring and the intermediate ring maintains the incision in an open configuration. If the thickness of the abdominal wall is less than the third length, then the fourth length will have to be selected.

The fourth length, which is less than the third length, is achieved by first pulling the intermediate ring 83f through the external ring 16f, and then pulling the intermediate ring 83f over the external ring 16f. The tension of the sheath 28f between the peritoneal ring 14f and the combination of the external ring 16f and the intermediate ring 83f, maintains the incision in an open configuration. This 3-ring retractor can therefore be positioned to effect four different lengths to accommodate variations in the thickness of the abdominal wall from patient to patient.

A most significant advantage associated with this embodiment is that the device enables a surgeon to retract and protectively line an abdominal wall incision while being able to easily adjust the device to accommodate variations from patient to patient in the thickness of the abdominal wall. The device is also very low in cost since it includes only four components, 3 rings 14f, 16f, and 83f, and a tubular sheath 28f.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A surgical wound retractor adapted to dilate a wound stretchable to a desired diameter, the retractor comprising:
   a first, distal ring having a diameter greater than the desired diameter of the wound and being adapted for disposition interiorly of the wound;
   a second, proximal ring having a diameter greater than the desired diameter of the wound and being adapted for disposition exteriorly of the wound;
   at least one retraction element having an outer surface and an inner surface, the retraction element being disposed in a generally cylindrical form between the first ring and the second ring to exert a radial retraction force on the wound, the retraction force being dependent on a distance separating the first ring and the second ring; and
   a base having a proximal side and a distal side, the base being adapted to be moved freely between the first ring and the second ring, the base including a sealing ring at the distal side of the base, the proximal side of the base including a recess adapted to receive the second ring and lock the second ring therein,
   wherein the second ring being adapted to be rolled such that the retraction element is rolled upon the second ring, and
   the second ring being adapted to be inserted into the recess on the proximal side of the base.

2. The surgical wound retractor recited in claim 1, the base being adapted receive a sealing cap.

* * * * *